US00PP15021P2

(12) United States Plant Patent
Vandenberg

(10) Patent No.: US PP15,021 P2
(45) Date of Patent: Jul. 20, 2004

(54) CHRYSANTHEMUM PLANT NAMED 'SOUND'

(50) Latin Name: *Chrysanthemum×morifolium*
Varietal Denomination: Sound

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 85 days.

(21) Appl. No.: 10/452,066

(22) Filed: Jun. 2, 2003

(51) Int. Cl.[7] ..... A01H 5/00
(52) U.S. Cl. ..... Plt./297
(58) Field of Search ..... Plt./297

*Primary Examiner*—Anne Marie Grunberg
(74) *Attorney, Agent, or Firm*—C. A. Whealy

(57) ABSTRACT

A distinct cultivar of Chrysanthemum plant named 'Sound', characterized by its upright plant habit; freely flowering habit; daisy-type inflorescences that are about 8 cm in diameter; attractive light purple-colored ray florets that resist fading and light green to bright yellow-colored disc florets; response time about 56 days; dark green-colored foliage; strong peduncles; and good postproduction longevity with inflorescences and foliage maintaining good substance and color for about 18 days in an interior environment.

2 Drawing Sheets

Botanical classification/cultivar designation: *Chrysanthemum×morifolium* cultivar Sound.

BACKGROUND OF THE INVENTION

The present invention relates to a new and distinct cultivar of Chrysanthemum plant, botanically known as *Chrysanthemum×morifolium* and hereinafter referred to by the name 'Sound'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross-pollination made by the Inventor in March, 1998, in Salinas, Calif., of a proprietary *Chrysanthemum×morifolium* seedling selection identified as code number K310, not patented, as the female, or seed, parent with a proprietary *Chrysanthemum×morifolium* seedling selection identified as K247, not patented, as the male, or pollen, parent.

The cultivar Sound was discovered and selected by the Inventor as a flowering plant within the progeny of the stated cross-pollination in a controlled environment in Alva, Fla., in March, 1999. The selection of this plant was based on its desirable inflorescence color and good form and substance.

Asexual reproduction of the new Chrysanthemum by terminal cuttings taken in a controlled environment in Alva, Fla. since June, 1999, has shown that the unique features of this new Chrysanthemum are stable and reproduced true to type in successive generations.

SUMMARY OF THE INVENTION

Plants of the cultivar Sound have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sound'. These characteristics in combination distinguish 'Sound' as a new and distinct cultivar:

1. Upright cut Chrysanthemum that is usually grown as a natural spray.
2. Freely flowering habit, about seven inflorescences per flowering stem.
3. Daisy-type inflorescences that are about 8 cm in diameter.
4. Attractive light purple-colored ray florets that resist fading and light green to bright yellow-colored disc florets.
5. Response time about 56 days.
6. Dark green foliage.
7. Strong peduncles.
8. Good postproduction longevity with inflorescences and foliage maintaining good substance and color for about 18 days in an interior environment.

Plants of the new Chrysanthemum can be compared to plants of the female parent selection. In side-by-side comparisons conducted in Alva, Fla., plants of the new Chrysanthemum differed from plants of the female parent selection in the following characteristics:

1. Plants of the new Chrysanthemum were taller than plants of the female parent selection.
2. Ray florets of plants of the new Chrysanthemum were darker purple in color than ray florets of plants of the female parent selection.

Plants of the new Chrysanthemum can be compared to plants of the male parent selection. In side-by-side comparisons conducted in Alva, Fla., plants of the new Chrysanthemum differed from plants of the male parent selection primarily in ray floret coloration as plants of the male parent selection had yellow-colored ray florets.

Plants of the new Chrysanthemum can also be compared to plants of the *Chrysanthemum×morifolium* cultivar Volare, disclosed in U.S. Plant Pat. No. 8,058. In side-by-side comparisons conducted in Alva, Fla., plants of the new Chrysanthemum differed from plants of the cultivar Volare in the following characteristics:

1. Plants of the new Chrysanthemum had larger and more uniform inflorescences than plants of the cultivar Volare.
2. Plants of the new Chrysanthemum had shorter peduncles than plants of the cultivar Volare.
3. Ray floret coloration of plants of the new Chrysanthemum was more uniform than ray floret coloration of plants of the cultivar Volare.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Sound' grown as a natural spray.

The photograph on the second sheet comprises a close-up view of a typical flowering stem of 'Sound' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in La Ceja, Antioquia, Colombia, South America, under conditions which approximate commercial practice in a single-layer polyethylene-covered greenhouse. Two-week old rooted cuttings were planted on Aug. 19, 2002 and received 14 long day/short nights followed by short day/long nights until flowering. Plants were grown as single-stem natural spray cut Chrysanthemums. During the production time, the following environmental conditions were measured: day temperatures, 20 to 27° C.; night temperatures, 8 to 13° C.; and light levels, 4,000 to 6,000 foot-candles. Measurements and numerical values represent averages for six to ten typical flowering stems and were taken about ten weeks after the start of short days.

Botanical classification: *Chrysanthemum×morifolium* cultivar Sound.

Commercial classification: Daisy-type cut Chrysanthemum.

Parentage:

*Female or seed parent.*—Proprietary *Chrysanthemum×morifolium* seedling selection identified as code number K310, not patented.

*Male or pollen parent.*—Proprietary *Chrysanthemum×morifolium* seedling selection identified as code number K247, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous daisy-type cut flower that is typically grown as a natural spray.

*Flowering stem description.*—Aspect: Erect. Length: About 122 cm. Diameter (natural spray diameter): About 16 cm. Diameter (base of stem): About 6.5 mm. Internode length: About 3.75 cm. Texture: Pubescent; longitudinally ridged. Color: 146A.

*Foliage description.*—Arrangement: Alternate. Length: About 5.5 cm. Width: About 3.2 cm. Apex: Mucronate. Base: Attenuate to truncate. Margin: Palmately lobed; sinuses parallel to divergent. Texture: Upper and lower surfaces pubescent; smooth and leathery; veins prominent on lower surface. Color: Developing and fully expanded foliage, upper surface: More green than 147A. Developing and fully expanded foliage, lower surface: More green than 147B. Venation, upper surface: 147A. Venation, lower surface: Close to 147B. Petiole: Length: About 1.2 cm. Diameter: About 3 mm. Color: Upper surface: 147A to 147B. Lower surface: Close to 146A.

Flowering description:

*Appearance.*—Daisy-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 56 days later when grown as a natural spray.

*Postproduction longevity.*—In an interior environment, inflorescences and foliage will maintain good color and substance for about 18 days in an interior environment.

*Quantity of inflorescences.*—Freely flowering habit, about seven inflorescences per stem develop.

*Inflorescence size.*—Diameter: About 8 cm. Depth (height): About 1.7 cm. Diameter of disc: About 1.9 mm. Diameter of receptacle: About 1 cm.

*Inflorescence buds.*—Shape: Oblate. Height: About 6 mm. Diameter: About 8 mm. Color: More green than 147A.

*Ray florets.*—Shape: Elongated oblong; slightly concave to flat. Length: About 4 cm. Width: About 1.3 cm. Corolla tube length: About 4 mm. Apex: Emarginate. Base: Fused. Texture: Smooth, velvety, glabrous; longitudinally ridged. Aspect: Initially upright; when mature, mostly perpendicular to peduncle; with development, slightly curved downward. Number of ray florets per inflorescence: About 32 arranged in about two rows. Color: When opening, upper surface: Close to 75A. When opening, lower surface: Close to 75D. Fully opened, upper surface: Close to 75A to 75B; color resists fading with development. Fully opened, lower surface: Close to 75D.

*Disc florets.*—Shape: Tubular, elongated. Length: About 7.5 mm. Width: Apex: About 2 mm. Base: About 1 mm. Number of disc florets per inflorescence: About 235. Color: Immature: Close to 144A. Mature: Apex: 154A to 9A. Mid-section: Close to 150C. Base: Close to 155D.

*Phyllaries.*—Quantity per inflorescence: About 30. Length: About 9 mm. Width: About 3 mm. Shape:

Lanceolate to deltoid. Apex: Acute. Base: Truncate. Margin: Entire. Texture, upper surface: Smooth, waxy. Texture, lower surface: Pubescent. Color, upper surface: Close to 146A. Color, lower surface: More green than 147A.

*Peduncles.*—Length: First peduncle: About 11 cm. Fourth peduncle: About 19.5 cm. Seventh peduncle: About 21.5 cm. Diameter: About 3 mm. Angle: About 40 to 45° from vertical. Strength: Very strong. Texture: Pubescent. Color: 146A.

*Reproductive organs.*—Androecium: Present on disc florets only. Anther color: 9A. Amount of pollen: None observed. Gynoecium: Present on both ray and disc florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'Sound', as illustrated and described.

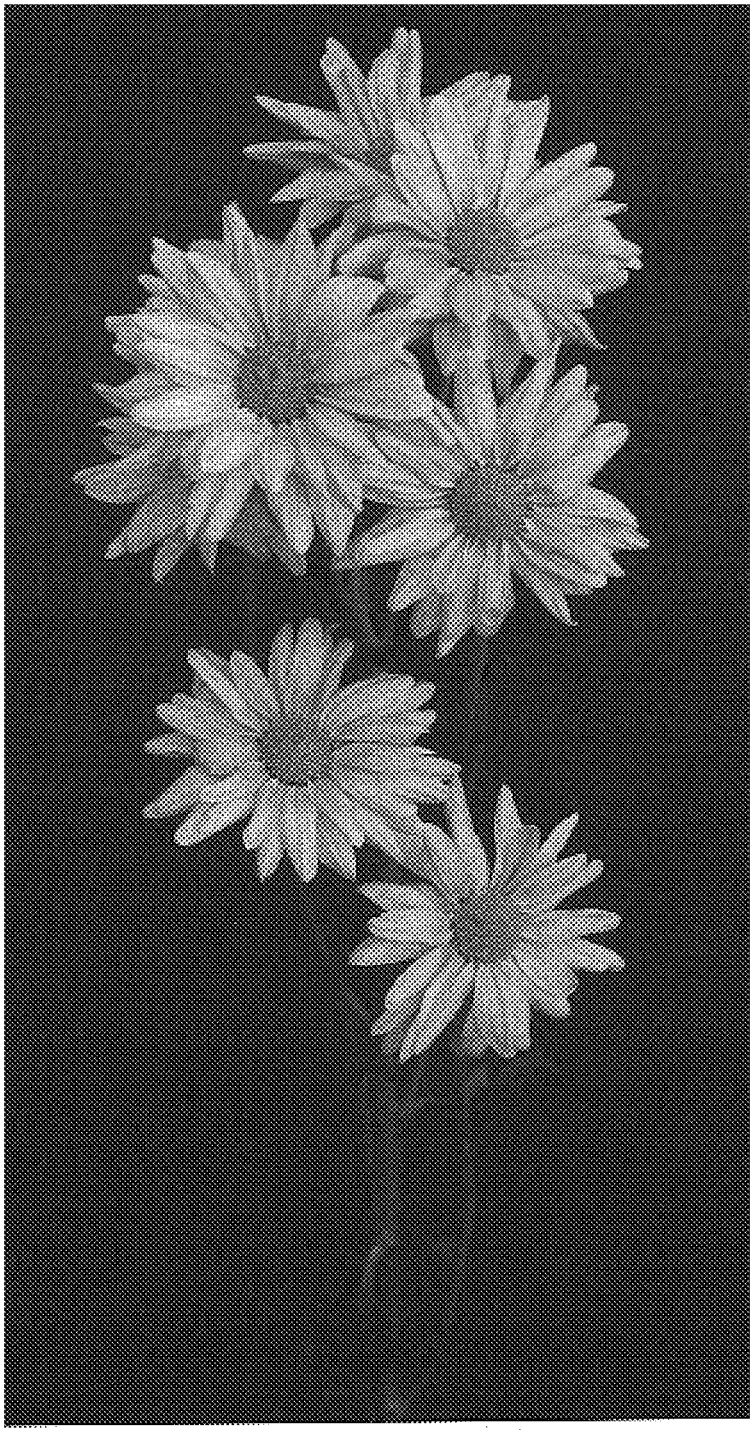

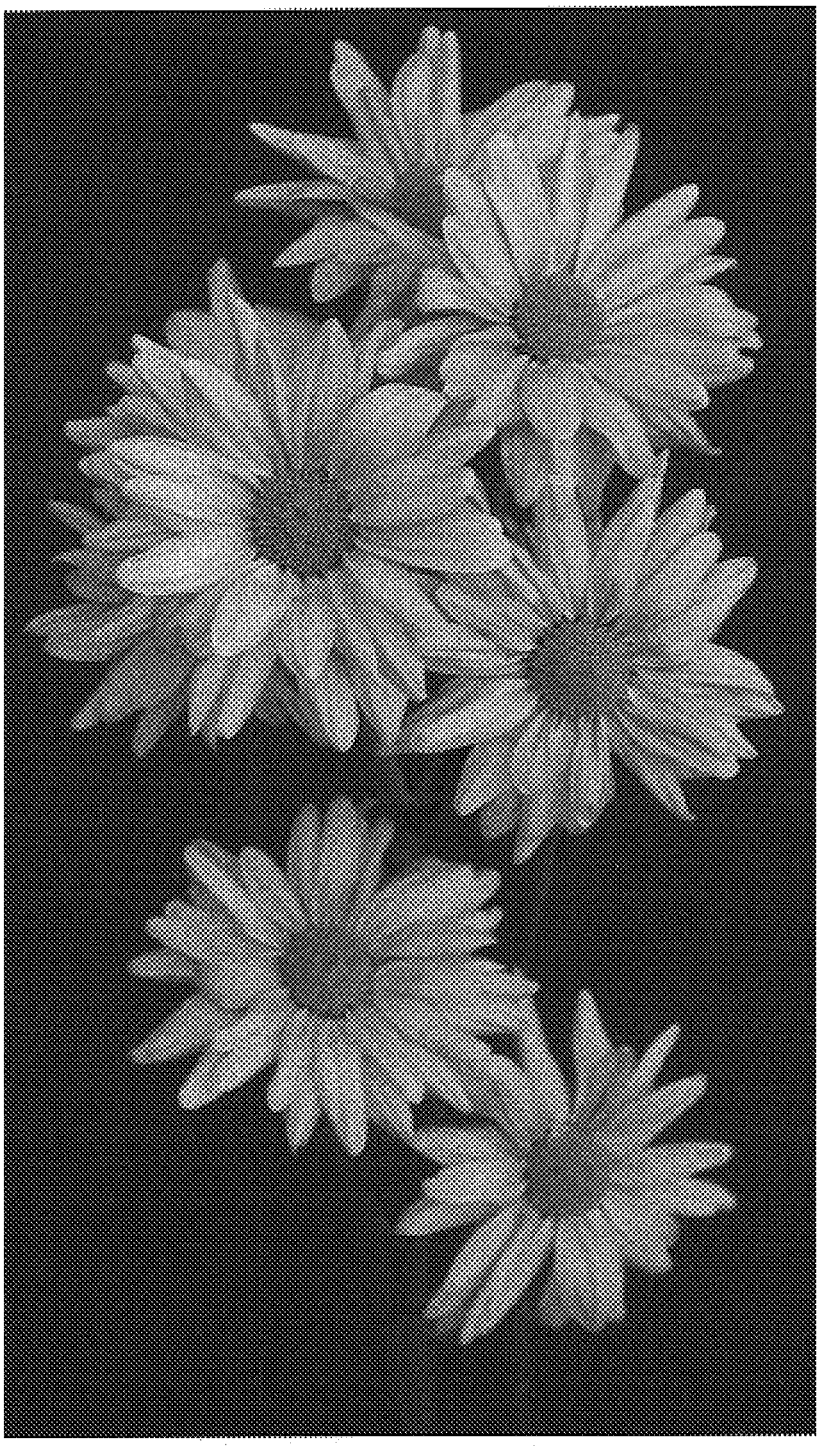

* * * * *